United States Patent [19]

Widler et al.

[11] Patent Number: 5,057,505

[45] Date of Patent: Oct. 15, 1991

[54] SUBSTITUTED AMINOMETHANEDIPHOSPHONIC ACIDS AND USE IN MEDICAMENTS

[75] Inventors: Leo Widler, Münchenstein; Knut Jaeggi, Basel, both of Switzerland

[73] Assignee: Ciba-Geigy Corporation, Ardsley, N.Y.

[21] Appl. No.: 354,053

[22] Filed: May 19, 1989

Related U.S. Application Data

[63] Continuation-in-part of Ser. No. 120,287, Nov. 13, 1987, abandoned.

[30] Foreign Application Priority Data

Nov. 21, 1986 [CH] Switzerland ......................... 4665/86
May 27, 1988 [CH] Switzerland ......................... 2005/88

[51] Int. Cl.$^5$ .................. A61K 31/675; C07F 9/6506; C07F 9/653; C07F 9/6539
[52] U.S. Cl. ........................................ 514/80; 514/93; 514/94; 514/95; 548/113; 548/119
[58] Field of Search .................. 548/113, 119; 514/80, 514/93, 94, 95

[56] References Cited

U.S. PATENT DOCUMENTS 4,687,767  8/1987  Bosies et al. .......................... 514/89

FOREIGN PATENT DOCUMENTS 186405  7/1986  European Pat. Off. .

OTHER PUBLICATIONS

Chem. Abstr. 93:181017z (1980).
Derwent Abstract of Japanese J55089-293 (1980).

*Primary Examiner*—Richard L. Raymond
*Attorney, Agent, or Firm*—JoAnn Villamizar

[57] ABSTRACT

Heteroarylaminomethanediphosphonic acids of the formula

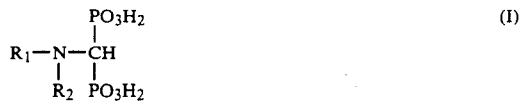

in which $R_1$ represents an optionally benzo- or cyclohexeno-fused 5-membered heteroaryl radical that contains, as hetero atom(s), either from 2 to 4 N-atoms or 1 or 2 N-atoms as well as 1 O-atom or S-atom and that is unsubstituted or is substituted by lower alkyl; by phenyl that is unsubstituted or is substituted by lower alkyl, lower alkoxy and/or by halogen; by lower alkoxy; by hydroxy; by di-lower alkylamino; by lower alkylthio and/or by halogen; and $R_2$ represents hydrogen or lower alkyl, and their salts, have a regulatory action on the calcium metabolism and can be used as active ingredients in medicaments for the treatment of illnesses that can be attributed to disorders of the calcium metabolism. They are manufactured, for example, as follows: in a compound of the formula

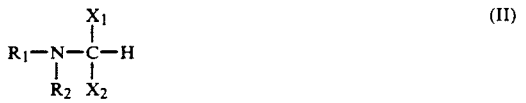

in which $X_1$ represents a functionally modified phosphono group X and $X_2$ represents phosphono or similarly represents a functionally modified phosphono group X, the group(s) X is(are) converted into free phosphono.

23 Claims, No Drawings

SUBSTITUTED AMINOMETHANEDIPHOSPHONIC ACIDS AND USE IN MEDICAMENTS

This is a continuation-in-part of our application Ser. No. 120,287 filed Nov. 13, 1987, now abandoned.

The invention relates to novel substituted aminomethanediphosphonic acids, especially heteroarylaminomethanediphosphonic acids of the formula

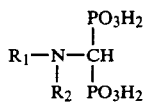

in which $R_1$ represents an optionally benzo- or cyclohexeno-fused 5-membered heteroaryl radical that contains, as hetero atom(s), either from 2 to 4 N-atoms or 1 or 2 N-atoms as well as 1 O-atom or S-atom and that is unsubstituted or is C-substituted by lower alkyl; by phenyl that is unsubstituted or is substituted by lower alkyl, lower alkoxy and/or by halogen; by lower alkoxy; by hydroxy; by di-lower alkylamino; by lower alkylthio and/or by halogen; and/or that is N-substituted by lower alkyl; or by phenyl-lower alkyl that is unsubstituted or is substituted by lower alkyl, lower alkoxy and/or by halogen; and $R_2$ represents hydrogen or lower alkyl, with the proviso that $R_2$ is other than hydrogen when $R_1$ represents a pyrazol-3-yl or isoxazol-3-yl radical that is optionally substituted by alkyl and/or by halogen, and their salts, to a process for the manufacture of the compounds according to the invention, to pharmaceutical preparations containing the latter and to their use as active ingredients in medicaments.

Optionally benzo- or cyclohexeno-fused 5-membered heteroaryl radicals containing, as hetero atom(s), either from 2 to 4 N-atoms or 1 or 2 N-atoms as well as 1 O-atom or S-atom are, for example, imidazolyl, for example imidazol-2-yl or -4-yl, thiazolyl, for example thiazol-2-yl, or also thiazol-5-yl or -4-yl, oxazolyl, for example oxazol-2-yl, or also oxazol-4-yl, triazolyl, for example 4H-1,2,4-triazol-3-yl or 2H-1,2,3-triazol-4-yl, tetrazolyl, for example tetrazol-5-yl, thiadiazolyl, for example 1,2,5-thiadiazol-3-yl, oxadiazolyl, for example 1,3,4-oxadiazol-2-yl, benzimidazolyl, for example benzimidazol-2-yl, benzoxazolyl, for example benzoxazol-2-yl, or benzothiazolyl, for example benzothiazol-2-yl. The radicals mentioned may contain one or several identical or different, especially one or two identical or different, substituents from among those mentioned at the beginning. Radicals $R_1$ having substitutable N-atoms are preferably N-substituted as indicated. Radicals $R_1$ are, for example, 1-$C_1$-$C_4$-alkylimidazol-2-yl radicals, such as 1-methylimidazol-2-yl, 1-phenyl-$C_1$-$C_4$-alkylimidazol-2-yl radicals, such as 1-benzylimidazol-2-yl, oxazol-2-yl, thiazol-2-yl, 4- and 5-$C_1$-$C_4$-alkylthiazol-2-yl radicals, such as 4- or 5-methylthiazol-2-yl, 5-phenylthiazol-2-yl, 1,2,4-thiadiazol-5-yl, 3-phenyl-1,2,4-thiadiazol-5-yl, 1,3,4-thiadiazol-2-yl, 5-methyl-1,3,4-thiadiazol-2-yl, benzoxazol-2-yl and benzothiazol-2-yl.

Hereinbelow, there is to be understood by lower radicals and compounds, for example, those containing up to and including 7, especially up to and including 4, C-atoms. In addition, the general terms have, for example, the following meanings:

Lower alkyl is, for example, $C_1$-$C_4$-alkyl, such as methyl, ethyl, propyl or butyl, or also iso-, sec.- or tert.-butyl, but may also be a $C_5$-$C_7$-alkyl group, such as a pentyl, hexyl or heptyl group.

Phenyl-lower alkyl is, for example, phenyl-$C_1$-$C_4$-alkyl, especially 1-phenyl-$C_1$-$C_4$-alkyl, such as benzyl.

Lower alkoxy is, for example, $C_1$-$C_4$-alkoxy, such as methoxy, ethoxy, propoxy, isopropoxy, butoxy, isobutoxy, sec.-butoxy or tert.-butoxy.

Di-lower alkylamino is, for example, di-$C_1$-$C_4$-alkylamino, such as dimethylamino, diethylamino, N-ethyl-N-methylamino, dipropylamino, N-methyl-N-propylamino or dibutylamino.

Lower alkylthio is, for example, $C_1$-$C_4$-alkylthio, such as methylthio, ethylthio, propylthio or butylthio, or also iso-, sec.- or tert.-butylthio.

Halogen is, for example, halogen having an atomic number of up to and including 35, such as fluorine, chlorine or bromine.

Salts of compounds of the formula I are especially the salts thereof with pharmaceutically acceptable bases, such as non-toxic metal salts derived from metals of groups Ia, Ib, IIa and IIb, for example alkali metal salts, especially sodium or potassium salts, alkaline earth metal salts, especially calcium or magnesium salts, copper salts, silver salts or zinc salts, or ammonium salts with ammonia or organic amines or quaternary ammonium bases, such as optionally C-hydroxylated aliphatic amines, especially mono-, di- or tri-lower alkylamines, for example methyl-, ethyl-, dimethyl- or diethyl-amine, mono-, di- or tri-(hydroxy-lower alkyl)-amines, such as ethanol-, diethanol- or triethanol-amine, tris(hydroxymethyl)amino-methane or 2-hydroxy-tert.-butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine, or quaternary aliphatic ammonium hydroxides, for example tetrabutylammonium hydroxide.

It should also be mentioned in this connection that the compounds of the formula I may be in the form of internal salts, for example of the formula

The mentioned compounds can accordingly also be converted, by treatment with a strongly protonic acid, such as with a hydrohalic acid, sulphuric acid, sulphonic acid, for example methane- or p-toluenesulphonic acid, or sulphamic acid, for example N-cyclohexylsulphamic acid, into the corresponding acid addition salts of the formula

in which $A^\ominus$ represents the anion of the protonic acid.

The compounds of the formula I and their salts have valuable pharmacological properties. In particular, they exhibit a pronounced regulatory action on the calcium metabolism of warm-blooded animals. In particular, in rats, they bring about pronounced inhibition of bone resorption, which can be demonstrated both in the test procedure according to Acta Endocrinol. 78, 613–24 (1975) by reference to the PTH-induced increase in the serum calcium level after subcutaneous administration in doses of from approximately 0.01 to approximately 1.0 mg/kg, and in the TPTX (thyroparathyroidectomised) rat model by reference to the experimental hypercalcaemia, induced by vitamin $D_3$, after the administration of doses of approximately from 0.001 to 1.0 mg s.c.. The tumour hypercalcaemia induced by Walker-256-tumours is likewise inhibited after peroral administration of from approximately 1.0 to approximately 100 mg/kg. Further, in adjuvant arthritis in rats in the test procedure according to Newbould, Brit. J. Pharmacology 21, 127 (1963) and according to Kaibara et al., J. Exp. Med. 159, 1388–96 (1984), they exhibit a marked inhibition of the progression of chronic arthritic processes in doses of approximately from 0.01 to 1.0 mg/kg s.c.. They are therefore excellently suitable as active ingredients in medicaments for the treatment of illnesses that can be attributed to calcium metabolism disorders, for example inflammatory processes in joints and degenerative processes in the arthrodial cartilage, of osteoporosis, periodontitis, hyperparathyroidism and of calcium deposits in blood vessels or on prosthetic implants. A favourable effect is produced both in illnesses in which an anomalous deposition of sparingly soluble calcium salts is to be observed, such as those from among the forms of arthritis, for example Morbus Bechterew, neuritis, bursitis, periodontitis and tendinitis, fibrodysplasia, osteoarthrosis and of artereosclerosis, and in those illnesses in which an anomalous degeneration of hard body tissue is well to the fore, such as hereditary hypophosphatasis, degenerative processes in the arthrodial cartilage, osteoporoses of various origins, Morbus Paget and osteodystrophia fibrosa, and also in tumour-induced osteolytic processes.

The invention relates especially to compounds of the formula I in which $R_1$ represents an imidazolyl, benzimidazolyl, 2H-1,2,3- or 4H-1,2,4-triazolyl, tetrazolyl, oxazolyl, benzoxazolyl, oxadiazolyl, thiazolyl, benzothiazolyl or thiadiazolyl radical that is C-unsubstituted or C-mono- or C-di-substituted by lower alkyl; by lower alkoxy; by phenyl that is unsubstituted or is mono- or di-substituted by lower alkyl, lower alkoxy and/or by halogen; by hydroxy; by di-lower alkylamino; by lower alkylthio and/or by halogen; and that is unsubstituted at a substitutable N-atom which may optionally be present or preferably N-mono- substituted by lower alkyl or by phenyl-lower alkyl that is unsubstituted or is mono- or di-substituted by lower alkyl, lower alkoxy and/or by halogen; and $R_2$ represents hydrogen or lower alkyl, and their salts, especially their internal salts and pharmaceutically acceptable salts with bases.

The invention relates especially, for example, to compounds of the formula I in which $R_1$ represents an imidazolyl, benzimidazolyl, 2H-1,2,3- or 4H-1,2,4-triazolyl, tetrazolyl, oxazolyl, benzoxazolyl, oxadiazolyl, thiazolyl, benzothiazolyl or thiadiazolyl radical that is unsubstituted or is mono- or di-substituted by lower alkyl; by lower alkoxy; by phenyl that is unsubstituted or is mono- or di-substituted by lower alkyl, lower alkoxy and/or by halogen; by hydroxy; by di-lower alkylamino; by lower alkylthio and/or by halogen; and $R_2$ represents hydrogen or lower alkyl, and their salts, especially their internal salts and pharmaceutically acceptable salts with bases.

The invention relates especially to compounds of the formula I in which $R_1$ represents a thiazolyl, such as thiazol-2-yl, radical, a benzothiazol-2-yl radical, a thiadiazolyl, such as 1,2,4-thiadiazol-5-yl or 1,3,4-thiadiazol-2-yl, radical, an oxazolyl, such as oxazol-2-yl, radical or a benzoxazol-2-yl radical each of which is unsubstituted or is C-substituted by $C_1$–$C_4$-alkyl, such as methyl, or by a phenyl radical that is unsubstituted or is mono- or di-substituted by $C_1$–$C_4$-alkyl, such as methyl, $C_1$–$C_4$-alkoxy, such as methoxy, and/or by halogen, such as chlorine; or represents an imidazolyl, such as imidazol-2-yl or imidazol-4-yl, radical or a benzimidazol-2-yl radical each of which is unsubstituted or is C-substituted by $C_1$–$C_4$-alkyl, such as methyl, or by a phenyl radical that is unsubstituted or is mono- or di-substituted by $C_1$–$C_4$-alkyl, such as methyl, $C_1$–$C_4$-alkoxy, such as methoxy, and/or by halogen, such as chlorine, and/or each of which is N-substituted by $C_1$–$C_4$-alkyl, such as methyl, or by a phenyl-$C_1$–$C_4$-alkyl radical, such as a benzyl radical, that is unsubstituted or is mono- or di-substituted by $C_1$–$C_4$-alkyl, such as methyl, $C_1$–$C_4$-alkoxy, such as methoxy, and/or by halogen, such as chlorine; and $R_2$ represents hydrogen, and their salts, especially their internal salts and pharmaceutically acceptable salts with bases.

The invention relates more especially to compounds of the formula I in which $R_1$ represents a thiazolyl, such as thiazol-2-yl or thiazol-4-yl, radical that is unsubstituted or is substituted by $C_1$–$C_4$-alkyl, such as methyl, by $C_1$–$C_4$-alkoxy, such as methoxy, by phenyl, by hydroxy, by di-$C_1$–$C_4$-alkylamino, such as dimethylamino or diethylamino, by $C_1$–$C_4$-alkylthio, such as methylthio, or by halogen having an atomic number of up to and including 35, such as chlorine, and $R_2$ represents hydrogen, and their salts, especially their internal salts and pharmaceutically acceptable salts with bases.

The invention relates even more especially to compounds of the formula I in which $R_1$ represents a thiazolyl, such as thiazol-2-yl, radical, a 1-$C_1$–$C_4$-alkyl-, such as 1-methyl-imidazol-2-yl or -4-yl, radical, or a phenyl-$C_1$–$C_4$-alkyl-, such as benzyl-imidazol-2-yl or -4-yl, radical each of which is unsubstituted or is C-substituted by $C_1$–$C_4$-alkyl, such as methyl, by $C_1$–$C_4$-alkoxy, such as methoxy, by phenyl, by hydroxy, by di-$C_1$–$C_4$-alkylamino, such as dimethylamino or diethylamino, by $C_1$–$C_4$-alkylthio, such as methylthio, or by halogen having an atomic number of up to and including 35, such as chlorine, and $R_2$ represents hydrogen, and their salts, especially their internal salts and pharmaceutically acceptable salts with bases.

The invention relates most especially to compounds of the formula I in which $R_1$ represents a thiazol-2-yl radical that is unsubstituted or is mono- or di-substituted, especially in the 4- and/or 5-position, by $C_1$–$C_4$-alkyl, such as methyl, or by phenyl, or represents an imidazol-2-yl or benzimidazol-2-yl radical that is unsubstituted or is mono-substituted in the 1-position by $C_1$–$C_4$-alkyl, such as methyl, or by phenyl-$C_1$–$C_4$-alkyl, such as benzyl, respectively, or represents an unsubstituted benzoxazol-2-yl or benzothiazol-2-yl radical, and $R_2$ represents hydrogen, and their salts, especially their internal salts and pharmaceutically acceptable salts with bases.

The invention relates specifically to the compounds of the formula I mentioned in the Examples and to their salts, especially their internal salts and pharmaceutically acceptable salts with bases.

The invention relates also to a process for the manufacture of compounds of the formula I and to their salts, which process is based on methods that are known per se. This process is characterised in that a) in a compound of the formula

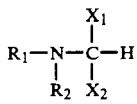 (II)

which is optionally intermediately protected at a substitutable N-atom of the radical $R_1$ and in which $X_1$ represents a functionally modified phosphono group X and $X_2$ represents phosphono or similarly represents a functionally modified phosphono group X, the group(s) X is(are) converted into free phosphono, or b) a compound of the formula

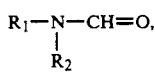 (III)

which is optionally intermediately protected at a substitutable N-atom of the radical $R_1$, is reacted first with phosphorus trioxide and then with water, and, if desired, in each case, a resulting compound is converted into a different compound of the formula I and/or a resulting free compound is converted into a salt or a resulting salt is converted into the free compound or into a different salt.

Functionally modified phosphono groups X that are to be converted into free phosphono according to process variant a) are, for example, in the form of an ester, especially in the form of a diester of the formula $$-P(=O)(OR)_2 \qquad (IIa)$$

in which OR represents, for example, lower alkoxy, or a phenoxy group that is optionally substituted by lower alkyl, lower alkoxy, halogen, trifluoromethyl and/or by hydroxy.

The conversion of a functionally modified phosphono group into a free phosphono group is effected in customary manner by hydrolysis, for example in the presence of a mineral acid, such as hydrochloric or hydrobromic acid or sulphuric acid, or by reaction with a tri-lower alkyl-halosilane, for example with trimethylchlorosilane or, especially, trimethyliodosilane or trimethylbromosilane, preferably while cooling, for example in a temperature range of from approximately 0° to approximately 25° C.

The starting materials of the formula II can be manufactured, for example, by condensing a compound of the formula

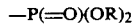 (IIb; $R_2$=H)

with at least the equimolar amount of an orthoformic acid triester of the formula $$H-C(OR)_3 \qquad (IIc)$$

in which OR represents, for example, lower alkoxy, or a phenoxy group that is optionally substituted by lower alkyl, lower alkoxy, halogen, trifluoromethyl and/or by hydroxy, there probably being formed initially a corresponding compound of the formula $$R_1-NH-CH(OR)_2 \qquad (IId1)$$

or $$R_1-N=CH-OR \qquad (IId2),$$

and by further reacting the condensation product with at least double the molar amount of a phosphorous acid diester, for example of the formula

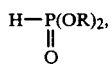 (IIe)

and, if desired, lower alkylating the resulting compound (II, $R_2$=H) to form the corresponding compound (II; $R_2$=lower alkyl).

In intermediates II in which the radical $R_1$ is N-substituted by lower alkyl or by phenyl-lower alkyl that is unsubstituted or is substituted by lower alkyl, lower alkoxy and/or by halogen, the N-substituent can be removed, lower alkyl being removed, for example, by treatment with a haloformic acid ester, such as a bromoformic or chloroformic acid lower alkyl ester, and subsequent hydrolysis of the resulting carbamate, and α-phenyl-lower alkyl radicals being removed, for example, by hydrogenolysis, for example by treatment with hydrogen in the presence of a hydrogenation catalyst, for example palladium-on-carbon and/or platinum oxide, or by reduction with a metal, for example by treatment with an alkali metal in ammonia.

It is also possible, however, to react the starting material IIb in a manner known per se with the phosphorous acid diester IIe in the presence of an orthoformic acid triester IIc without isolating the intermediate stage. Thus, according to an especially preferred embodiment, the corresponding compound IIb is reacted at boiling heat in the presence of at least the equimolar amount of an orthoformic acid triester IIc with at least double the molar amount of the phosphorous acid diester IIe without isolating the intermediate stage, for example of the formula IId1 or IId2, and the primary product II is hydrolysed by treatment with aqueous hydrochloric acid at boiling heat.

The reaction of compounds III with phosphorus trioxide according to process variant b) is preferably effected with the latter being formed in situ, for example by reacting phosphorus trichloride and phosphorous acid at elevated temperature, for example at approximately from 50° to 65° C., adding the reactant III, heating further and working up the primary product, a 1:1 adduct of the aldehyde of the formula

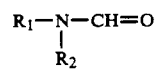 (III)

with phosphorus trioxide of hitherto-unknown structure, by hydrolysis, preferably by treatment with water.

In a modification of this preferred embodiment of process variant b), orthophosphoric acid is reacted, at approximately from 50° C. to 70° C., with an approximately 1.1- to approximately 2-fold, preferably approximately 1.5-fold, excess of phosphorus trichloride, the reactant III is added, the whole is heated for a prolonged period at approximately from 50° C. to 70° C., diluted with 80% phosphoric acid and worked up by hydrolysis.

Starting materials III can be manufactured in customary manner, for example by reacting an amine of the formula

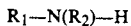  (IIb; R=H)

with formic acid or a functional carboxy derivative thereof, for example with a formic acid ester of the formula

  (IIe)

in which OR represents, for example, a phenoxy group that is optionally substituted by lower alkyl, lower alkoxy, halogen, trifluoromethyl and/or by hydroxy, or with formamide.

For the intermediate protection of a substitutable N-atom of the radical $R_1$ the customary N-protecting groups and methods of introducing and removing them are suitable, for example 2,2,2-trihaloethoxycarbonyl radicals, such as 2,2,2-triiodo-, 2,2,2-tribromo- or 2,2,2-trichloro-ethoxycarbonyl radicals, which can be removed, for example, by treatment with zinc in acetic acid, α-phenyl-lower alkoxycarbonyl radicals, such as benzyloxycarbonyl, which can be removed, for example, by catalytic hydrogenation, and lower alkanesulphonyl groups, such as methanesulphonyl, which can be removed, for example, by treatment with bis(2-methoxyethoxy)-sodium aluminium hydride, and also, however, α-phenylalkyl or alkyl groups, the removal of which is dealt with hereinafter.

Compounds of the formula I obtained in accordance with the process of the invention or by another process that is known per se can be converted into other compounds of the formula I in a manner known per se.

For example, lower alkyl $R_2$ can be introduced into compounds of the formula I in which $R_2$ represents hydrogen by reaction with a reactive ester, such as a hydrohalic acid ester or an organic sulphonic acid ester, of a lower alkanol. It is also possible, however, to introduce an aliphatic radical, for example methyl, by reaction with an aliphatic aldehyde, for example with formaldehyde and formic acid.

It is also possible in compounds of the formula I in which the radical $R_1$ is N-substituted by lower alkyl or by phenyl-lower alkyl that is unsubstituted or is substituted by lower alkyl, lower alkoxy and/or by halogen, to remove the N-substituent, lower alkyl being removed, for example, by treatment with a haloformic acid ester, such as a bromoformic or chloroformic acid lower alkyl ester, and subsequent hydrolysis of the resulting carbamate, and α-phenyl-lower alkyl radicals being removed, for example, by hydrogenolysis, for example by treatment with hydrogen in the presence of a hydrogenation catalyst, for example palladium-on-carbon and/or platinum oxide, or by reduction with a metal, for example by treatment with an alkali metal in ammonia.

Resulting free compounds of the formula I, including their internal salts of the formula I', can be converted into salts with bases by partial or complete neutralisation with one of the bases mentioned at the beginning. Acid addition salts of the formula I'' also can be converted in an analogous manner into the corresponding free compounds of the formula I or internal salts of the formula I'.

Conversely, resulting free compounds of the formula I can be converted into acid addition salts of the formula I'' by treatment with one of the protonic acids mentioned at the beginning.

Resulting salts can be converted into the free compounds in a manner known per se, for example by treatment with an acid reagent, such as a mineral acid, or, as the case may be, with a base, for example alkali liquor.

The compounds, including their salts, may also be obtained in the form of their hydrates or may include the solvent used for crystallisation.

Owing to the close relationship between the novel compounds in free form and in the form of their salts, hereinbefore and hereinafter there is to be understood by the free compounds or their salts, where appropriate and expedient, optionally also the corresponding salts or free compounds, respectively.

The invention relates also to those embodiments of the process according to which a compound obtainable as an intermediate at any stage of the process is used as starting material and the remaining steps are carried out or a starting material in the form of a salt and/or racemate or antipode is used or especially is formed under the reaction conditions.

The starting materials that are used in the process of the present invention are preferably those which result in the compounds described at the beginning as being especially valuable. The invention relates also to novel starting materials and processes for the manufacture thereof.

The invention relates also to pharmaceutical compositions containing, as the active ingredient, a known compound of the formula I, wherein $R_2$ represents a pyrazol-3-yl or isoxazol-3-yl radical that is unsubstituted or mono- or disubstituted by lower alkyl and/or halogen and $R_2$ denotes hydrogen, specifically 1-(isoxazol-3-ylamino)methane-1,1-diphosphonic acid, 1-(4-methylisoxazol-3-ylamino)methane-1,1-diphosphonic acid, 1-(5-methylisoxazol-3-ylamino)methane-1,1-diphosphonic acid, 1-(pyrazol-3-ylamino)methane-1,1-diphosphonic acid, 1-(4-methylpyrazol-3-ylamino)methane-1,1-diphosphonic acid or 1-(5-methylpyrazol-3-ylamino)methane-1,1-diphosphonic acid or a pharmaceutically acceptable salt thereof, to the use of the active ingredient as a medicament and to a method of treatment of illnesses associated with calcium metabolism disorders.

The pharmaceutical preparations according to the invention, which contain compounds of the formula I or pharmaceutically acceptable salts thereof, are for enteral, such as oral or rectal, and parenteral administration and contain the pharmacological active ingredient on its own or together with a pharmaceutically acceptable carrier. The dosage of the active ingredient depends upon the species of warm-blooded animal, its age and individual condition and also on the mode of administration. In a normal case, the estimated approximate daily dose for a warm-blooded animal of approximately 75 kg body weight is approximately from 20 to 1000 mg, preferably approximately from 30 to 300 mg, in the case of oral administration and approximately from 1 to 25 mg, preferably approximately from 1 to 10 mg, in the case of intravenous administration, the dose advantageously being divided into several equal partial doses.

The novel pharmaceutical preparations contain, for example, from approximately 10% to approximately 80%, preferably from approximately 20% to approximately 60%, active ingredient. Pharmaceutical preparations according to the invention for enteral and parenteral administration are, for example, those in dosage unit form, such as dragées, tablets, capsules or suppositories, and also ampoules. These are prepared in a manner known per se, for example by means of conventional mixing, granulating, confectioning, dissolving or lyophilising processes. For example, pharmaceutical preparations for oral administration can be obtained by combining the active ingredient with solid carries, if desired granulating a resulting mixture and, if desired or necessary, processing the mixture or granulate, after the addition of suitable adjuncts, into tablets or dragée cores.

Suitable carries are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatine, tragacanth, methylcellulose and/or polyvinylpyrrolidone, and/or, if desired, disintegrators, such as the above-mentioned starches, carboxymethyl starch, crosslinked polyvinylpyrrolidone, agar, alginic acid or a salt thereof, such as sodium alginate. Adjuncts are especially flow-regulating and lubricating agents, for example silica, talc, stearic acid or salts thereof, such as magnesium or calcium stearate, and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures, or, for the preparation of coatings that are resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Other orally administrable pharmaceutical preparations are dry-filled capsules consisting of gelatine, and also soft sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, it being possible also to add stabilisers.

Suitable rectally administrable pharmaceutical preparations are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatine rectal capsules that contain a combination of the active ingredient with a base material; suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, or suspensions of the active ingredient, such as corresponding oily injection suspensions in which suitable lipophilic solvents or vehicles, such as fatty oils, for example sesame oil, or synthetic fatty acid esters, for example ethyl oleate or triglycerides, are used, or aqueous injection suspensions that contain vicosity-increasing substances, for example sodium carboxymethylcellulose, sorbitol and/or dextran and, if desired, also stabilisers.

The present invention relates also to the use of the compounds of the formula I and their salts, preferably for the treatment of illnesses that can be attributed to calcium metabolism disorders, for example of the rheumatic type, and especially of osteoporoses.

Dosages under 0.01 mg/kg body weight have only a negligible effect on pathological calcification or the degeneration of hard tissue. At dosages above 100 mg/kg body weight, toxic side-effects may occur in long-term use. The compounds of the formula I and their salts can be administered both orally and, in the form of a hypertonic solution, subcutaneously, intramuscularly or intravenously. The preferred daily doses are in the range of approximately from 0.1 to 5 mg/kg in the case of oral administration, in the range of approximately from 0.1 to 1 mg/kg in the case of subcutaneous and intramuscular administration and in the range of approximately from 0.01 to 2 mg/kg in the case of intravenous administration.

The dosage of the compounds used is, however, variable and depends on the particular conditions, such as nature and severity of the illness, duration of treatment and on the particular compound. Single doses contain, for example, from 0.01 to 10 mg, dosage unit forms for parenteral, such as intravenous, administration contain, for example, from 0.01 to 0.1 mg, preferably 0.02 to 0.08 mg, and oral dosage unit forms contain, for example, from 0.2 to 2.5 mg, preferably from 0.3 to 1.5 mg, per kg of body weight. The preferred individual dosage for oral administration is from 10 to 100 mg and for intravenous administration from 0.5 to 5 mg and can be administered in up to 4 single doses per day. The higher dosages in the case of oral administration are necessary owing to the limited resorption. In the case of long-term treatments, the initially higher dosage can normally be converted to low dosages while still maintaining the desired effect.

The following Examples illustrate the invention described above; they are not intended, however, to limit the scope thereof in any way. Temperatures are given in degrees Celsius.

EXAMPLE 1

6.57 g (17 mmol) of 1-(thiazol-2-ylamino)-methane-1,1-diphosphonic acid tetraethyl ester are dissolved in 70 ml of N hydrochloric acid and heated under reflux for 6 hours. In the course of the reaction, the product separates out in the form of a fine white precipitate. After cooling to room temperature, filtration is carried out and the product is washed with aqueous methanol. 4.33 g (93% of the theoretical yield) of 1-(thiazol-2-ylamino)methane-1,1-diphosphonic acid of m.p. 275° (decomposition) are obtained.

The starting material can be prepared, for example, in the following manner:

A mixture consisting of 10.0 g (0.1 mol) of 2-aminothiazole, 20.0 ml (0.12 mol) of orthoformic acid triethyl ester and 26.6 ml (0.2 mol) of diethyl phosphite is heated under reflux for 1 hour. The ethanol liberated is distilled off, the internal temperature gradually increasing to approximately 150°. The residue is taken up in chloroform and filtered over silica gel. The crude product is purified by column chromatography (silica gel/ethyl acetate). 4.37 g (11% of the theoretical yield) of 1-(thiazol-2-ylamino)-methane-1,1-diphosphonic acid tetraethyl ester of m.p. 103°-104° are obtained.

EXAMPLE 2

In a manner analogous to that described in Example 1 it is also possible to prepare 1-(oxazol-2-ylamino)methane-1,1-diphosphonic acid of m.p. 245° (decomposition) and 1-(benzoxazol-2-ylamino)methane-1,1-diphosphonic acid of m.p. 270° (decomposition).

EXAMPLE 3

4.36 g (10 mmol) of 1-(benzothiazol-2-ylamino)methane-1,1-diphosphonic acid tetraethyl ester are heated in 40 ml of N hydrochloric acid at 110°-120° for 6 hours. In the course of the reaction, the product separates out in the form of a white precipitate. After cooling to room temperature, filtration is carried out and the product is washed with aqueous methanol. 3.09 g (95% of the theoretical yield) of 1-(benzothiazol-2-ylamino)methane-1,1-diphosphonic acid of m.p. 290° (decomposition) are obtained.

The starting material can be prepared, for example, in the following manner:

A mixture consisting of 3.0 g (20 mmol) of 2-aminobenzothiazole, 4.0 ml (24 mmol) of orthoformic acid triethyl ester and 5.3 ml (40 mmol) of diethyl phosphite is heated at 120°-125° for 5 hours. The yellow precipitate which separates out at the beginning of the reaction gradually goes into solution again. The ethanol liberated is distilled off during the reaction. The crude product, which solidifies on being left to stand, is purified by column chromatography (silica gel/ethyl acetate/methanol). 5.62 g (64% of the theoretical yield) of 1-(benzothiazol-2-ylamino)methane-1,1-diphosphonic acid tetraethyl ester of m.p. 165°-167° are obtained.

EXAMPLE 4

1.30 g (3.2 mmol) of 1-(4-methylthiazol-2-ylamino)methane-1,1-diphosphonic acid tetraethyl ester are heated in 20 ml of 1N hydrochloric acid at 100° for 20 hours. After cooling, 20 ml of methanol are added. During subsequent stirring, the product separates out in the form of fine white crystals. The filtrate is subsequently washed with methanol and petroleum ether. Yield: 615 mg (67% of the theoretical yield) of 1-(4-methylthiazol-2-ylamino)methane-1,1-diphosphonic acid of m.p. 294° (decomposition).

The starting material can be prepared, for example, in the following manner:

A mixture consisting of 2.33 g (20 mmol) of 2-amino-4-methylthiazole, 4.0 ml (24 mmol) of orthoformic acid triethyl ester and 5.3 ml (40 mmol) of diethyl phosphite is heated at 120°-125° for 4 hours. The ethanol liberated is distilled off. The residue is purified by column chromatography (silica gel/ethyl acetate/methanol). 1.32 g (17% of the theoretical yield) of 1-(4-methylthiazol-2-ylamino)methane-1,1-diphosphonic acid tetraethyl ester are obtained in the form of a viscous oil.

EXAMPLE 5

1.97 g (4.9 mmol) of 1-(5-methylthiazol-2-ylamino)methane-1,1-diphosphonic acid tetraethyl ester are heated under reflux in 20 ml of N hydrochloric acid for 6 hours. Upon cooling and leaving the reaction mixture to stand at room temperature, the product crystallises. It is filtered and washed with acetone and petroleum ether. Yield: 0.64 g (45% of the theoretical yield) of 1-(5-methylthiazol-2-ylamino)-methane-1,1-diphosphonic acid of m.p. 208° (decomposition).

The starting material can be prepared, for example, in the following manner:

A mixture consisting of 1.14 g (10 mmol) of 2-amino-5-methylthiazole, 2.0 ml (12 mmol) of orthoformic acid triethyl ester and 2.65 ml (20 mmol) of diethyl phosphite is heated at 120°-125° for 4½ hours. The ethanol liberated is distilled off. The residue is purified by column chromatography (silica gel/ethyl acetate/methanol). 1.97 g (49% of the theoretical yield) of 1-(5-methylthiazol-2-ylamino)methane-1,1-diphosphonic acid tetraethyl ester are obtained in the form of a viscous oil.

EXAMPLE 6

4.02 g (8.7 mmol) of 1-(5-phenylthiazol-2-ylamino)methane-1,1-diphosphonic acid tetraethyl ester are heated under reflux in 30 ml of N hydrochloric acid for 18 hours. After cooling to room temperature, a small quantity of methanol is added and the whole is filtered. The filtrate is heated under reflux in methanol for 1 hour, filtered while hot and washed twice with hot methanol. Yield: 2.90 g (95% of the theoretical yield) of 1-(5-phenylthiazol-2-ylamino)methane-1,1-diphosphonic acid of m.p. 290° (decomposition).

The starting material can be prepared, for example, in the following manner:

A mixture consisting of 2.93 g (16.6 mmol) of 2-amino-5-phenylthiazole, 3,3 ml (19,9 mmol) of orthoformic acid triethyl ester and 4,4 ml (33,5 mmol) of diethyl phosphite is heated first for 2 hours at 120° and then for 2 hours at 130°. The ethanol liberated is distilled off in the course of the reaction. The product, which solidifies upon cooling, is purified by chromatography (silica gel/ethyl acetate/methanol). 4.12 g (54% of the theoretical yield) of 1-(5-phenylthiazol-2-ylamino)methane-1,1-diphosphonic acid tetraethyl ester of m.p. 151°-153° are obtained.

EXAMPLE 7

2.5 g (5.96 mmol) of 1-(benzimidazol-2-ylamino)methane-1,1-diphosphonic acid tetraethyl ester are dissolved in 25 ml of 1N hydrochloric acid and heated at 100°-110° for 26 hours. In the course of the reaction, the product separates out in the form of a fine white precipitate. It is filtered while hot and washed with water and then with methanol. 0.23 g (13% of the theoretical yield) of 1-(benzimidazol-2-ylamino)methane-1,1-diphosphonic acid of m.p. 265° (decomposition) is obtained.

The starting material can be prepared, for example, in the following manner:

6.66 g (50 mmol) of 2-aminobenzimidazole, 10.0 ml (60 mmol) of orthoformic acid triethyl ester and 13.3 ml (101 mmol) of diethyl phosphite are mixed together and then stirred for 2 hours at 125°-130° until no more ethanol is distilled off. The residue is purified by column chromatography (silica gel/ethyl acetate/-methanol, 9:1). 2.89 g (14% of the theoretical yield) of 1-(benzimidazol-2-ylamino)methane-1,1-diphosphonic acid tetraethyl ester of m.p. 169°-170° are obtained.

EXAMPLE 8

7 g of phosphorus trichloride are mixed with 4.0 g of phosphorous acid and the mixture is heated, while stirring, at 60° for 1 hour. 6.12 g of N-(thiazol-2-yl)formamide are added thereto and the mixture is heated for a further 6 hours at approximately 60°. The mixture is then stirred with 30 ml of water, filtered with suction, subsequently washed with aqueous methanol and dried under reduced pressure. 2.0 g of 1-(thiazol-2-ylamino)methane-1,1-diphosphonic acid of m.p. 275° (decomposition) are obtained.

EXAMPLE 9

2.0 g (20.4 mmol) of crystalline orthophosphoric acid are stirred with 3.5 g (25.5 mmol) of phosphorus trichloride for 1 hour at 55°-60°. 4.8 g (20.0 mmol) of N-(4-phenylthiazol-2-yl)formamide are then added thereto. The reaction mixture is left to stand for approximately 24 hours at 60°. For dilution, 10 ml of 80% phosphoric acid are added thereto and the whole is left to stand overnight at room temperature. It is then heated again to 60°-70° and a further 1.37 g (10 mmol) of phosphorus trichloride are added thereto, the whole is further stirred for 2 hours at 60°-70°, 30 ml of water and 20 ml of acetone are added and the whole is stirred for 2 hours at 60° to complete the reaction. The reaction mixture is allowed to cool to room temperature, and the fine, pale yellow precipitate is filtered off and washed with water-/acetone 3:2. The residue is purified by being boiled once with water/acetone 1:1 and twice with methanol. 180 mg (2.6% of the theoretical yield) of 1-(4-phenylthiazol-2-ylamino)methane-1,1-diphosphonic acid of m.p. 298° (decomposition) are obtained.

The starting material can be prepared, for example, in the following manner:

13.22 g (75 mmol) of 2-amino-4-phenylthiazole are heated at 110° for 5 hours with 40 ml of formic acid. The reaction mixture is cooled to room temperature and poured onto ice. The white precipitate which separates out is filtered and washed with ice-water. The product is purified by means of petroleum ether. 7.01 g (45.8% of the theoretical yield) of 4-(phenylthiazol-2-yl-amino)formamide of m.p. 161°-164° are obtained.

EXAMPLE 10

2.74 g of 1-(thiazol-2-ylamino)methane-1,1-diphosphonic acid (example 1 ) are suspended in 10 ml of water. While stirring, 10 ml of 2N aqueous sodium hydroxide solution are added dropwise to the suspension. The resulting solution is evaporated to dryness. 40 ml of methanol are added to the resulting viscous residue and the mixture is stirred thoroughly. The resulting crystalline precipitate is filtered off and dried, yielding the disodium 1-(thiazol-2-ylamino)methane-1,1-diphosphonate of the formula

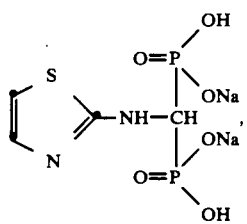

(XI)

which has a melting point of more than 320°.

EXAMPLE 11

In a manner analogous to that described in example 10, it is also possible to prepare the following:

disodium 1-(oxazol-2-ylamino)methane-1,1-diphosphonate;
disodium 1-(benzoxazol-2-ylamino)methane-1,1-diphosphonate;
disodium 1-(benzothiazol-2-ylamino)methane-1,1-diphosphonate;
disodium 1-(4-methylthiazol-2-ylamino)methane-1,1-diphosphonate;
disodium 1-(5-methylthiazol-2-ylamino)methane-1,1-diphosphonate;
disodium 1-(5-phenylthiazol-2-ylamino)methane-1,1-diphosphonate;
disodium 1-(benzimidazol-2-ylamino)methane-1,1-diphosphonate; and
disodium 1-(4-phenylthiazol-2-ylamino)methane-1,1-diphosphonate.

EXAMPLE 12

0.954 mg of 1-(thiazole-2-ylamino)methane-1,1-diphosphonic acid (example 1) are dissolved in 10 ml of water. A solution of 1.018 g of silver nitrate in 5 ml of water is added dropwise, while stirring. The mixture is then stirred for another 30 minutes. The precipitate is filtered off and washed successively with methanol and diethyl ether, yielding the disilver 1-(thiazol-2-ylamino)-methane-1,1-diphosphonate, which has a melting point of more than 320°.

EXAMPLE 13

In a manner known per se, for example as described in Examples 1 to 10, it is also possible to prepare the following:

1-(imidazol-2-ylamino)methane-1,1-diphosphonic acid,
1-(imidazol-4-ylamino)methane-1,1-diphosphonic acid,
1-(1-methylimidazol-2-ylamino)methane-1,1-diphosphonic acid,
1-(tetrazol-5-ylamino)methane-1,1-diphosphonic acid,
1-(oxazol-2-ylamino)methane-1,1-diphosphonic acid, m.p. 245° (decomposition),
1-(1,3,4-thiadiazol-2-ylamino)methane-1,1-diphosphonic acid, m.p. 289° (decomposition),
1-(5-methyl-1,3,4-thiadiazol-2-ylamino)methane-1,1-diphosphonic acid, m.p. 195° (decomposition),
1-(3-phenyl-1,2,4-thiadiazol-5-ylamino)methane-1,1-diphosphonic acid, m.p. 251° (decomposition),
1-[N-(thiazol-2-yl)-N-methyl-amino]methane-1,1-diphosphonic acid, m.p. 263° (decomposition),
1-(1,2,4-thiadiazol-5-ylamino)methane-1,1-diphosphonic acid, m.p. 230° (decomposition),
1-[N-(thiazol-2-yl)-N-(n-butyl)-amino]methane-1,1-diphosphonic acid, m.p. 173°,
1-[N-(5-methylthiazol-2-yl)-N-methyl-amino]methane-1,1-diphosphonic acid,
1-[N-(5-methylthiazol-2-yl)-N-(n-butyl)-amino]methane-1,1-diphosphonic acid,
1-(1-methyl-4H-1,2,4-triazol-5-ylamino)methane-1,1-diphosphonic acid,
1-(5-methylthiazol-4-ylamino)methane-1,1-diphosphonic acid,
1-(1,5-dimethylimidazol-2-ylamino)methane-1,1-diphosphonic acid,
1-(1,2,4-oxadiazol-3-ylamino)methane-1,1-diphosphonic acid, 1-(1,3,4-oxadiazol-2-ylamino)methane-1,1-diphosphonic acid,
1-(5-chlorothiazol-2-ylamino)methane-1,1-diphosphonic acid, m.p. 191°,
1-(1-methylpyrazol-4-ylamino)methane-1,1-diphosphonic acid,
1-(5-but-1-ylthiazol-2-ylamino)methane-1,1-diphosphonic acid, m.p. 267° (decomposition),
1-(5-prop-1-ylthiazol-2-ylamino)methane-1,1-diphosphonic acid, m.p. 275° (decomposition),
1-(5-prop-2-ylthiazol-2-ylamino)methane-1,1-diphosphonic acid, m.p. 255° (decomposition), and
1-(5-ethylthiazol-2-ylamino)methane-1,1-diphosphonic acid, m.p. 243° (decomposition),
and the disodium salts thereof.

EXAMPLE 14

Tablets, each containing 50 mg of active ingredient, for example 1-(thiazol-2-ylamino)methane-1,1-diphosphonic acid or a salt, for example the sodium salt, thereof, can be prepared in the following manner:

| Constituents (for 1000 tablets) | |
|---|---|
| active ingredient | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralised water | q.s. |

Preparation

All the solid ingredients are first forced through a sieve of 0.6 mm mesh width. Then the active ingredient, the lactose, the talc, the magnesium stearate and half of the starch are mixed. The other half of the starch is suspended in 40 ml of water and this suspension is added to a boiling solution of the polyethylene glycol in 100 ml of water. The resulting paste is added to the pulverulent substances and the mixture is granulated, if necessary with the addition of water. The granulate is dried overnight at 35°, forced through a sieve of 1.2 mm mesh width and compressed to form tablets of approximately 6 mm diameter which are concave on both sides.

EXAMPLE 15

Tablets, each containing 100 mg of active ingredient, for example 1-(thiazol-2-ylamino)methane-1,1-diphosphonic acid or a salt, for example the sodium salt, thereof, can be prepared in the following manner:

| Constituents (for 1000 tablets) | |
|---|---|
| active ingredient | 100.0 g |
| lactose | 100.0 g |
| wheat starch | 47.0 g |
| magnesium stearate | 3.0 g |

Preparation

All the solid ingredients are first forced through a sieve of 0.6 mm mesh width. Then the active ingredient, the lactose, the magnesium stearate and half of the starch are mixed. The other half of the starch is suspended in 40 ml of water and this suspension is added to 100 ml of boiling water. The resulting paste is added to the pulverulent substances and the mixture is granulated, if necessary with the addition of water. The granulate is dried overnight at 35°, forced through a sieve of 1.2 mm mesh width and compressed to form tablets of approximately 6 mm diameter which are concave on both sides.

EXAMPLE 16

In a manner analogous to that described in Examples 14 and 15, it is also possible to prepare tablets each containing 100 mg or 50 mg of another of the compounds of the formula I mentioned in Examples 1 to 13, which compounds may also be in the form of salts with bases, for example in the form of the disodium salt.

EXAMPLE 17

Tablets for chewing, each containing 75 mg of active ingredient, for example 1-(thiazol-2-ylamino)methane-1,1-diphosphonic acid or a salt, for example the sodium salt, thereof, can be prepared, for example, in the following manner:

| Composition: (for 1000 tablets) | |
|---|---|
| active ingredient | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatine solution | q.s. |

Preparation

All the solid ingredients are first forced through a sieve of 0.25 mm mesh width. The mannitol and the lactose are mixed, granulated with the addition of gelatine solution, forced through a sieve of 2 mm mesh width, dried at 50° and again forced through a sieve of 1.7 mm mesh width. The active ingredient, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

In an analogous manner, it is also possible to prepare tablets each containing 75 mg of another of the compounds of the formula I mentioned in Examples 1 to 13, which compounds may also be in the form of salts with bases, for example in the form of the disodium salt.

EXAMPLE 18

Tablets, each containing 10 mg of active ingredient, for example 1-(thiazol-2-ylamino)methane-1,1-diphosphonic acid or a salt, for example the sodium salt, thereof, can be prepared in the following manner:

| Composition (for 1000 tablets) | |
|---|---|
| active ingredient | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralised water | q.s. |

Preparation

The solid ingredients are first forced through a sieve of 0.6 mm mesh width. Then the active ingredient, lactose, talc, magnesium stearate and half of the starch are intimately mixed. The other half of the starch is suspended in 65 ml of water and this suspension is added to a boiling solution of the polyethylene glycol in 260 ml of water. The resulting paste is added to the pulverulent substances, and the whole is mixed and granulated, if necessary with the addition of water. The granulate is dried overnight at 35°, forced through a sieve of 1.2 mm mesh width and compressed to form tablets of approximately 10 mm diameter which are concave on both sides and have a breaking notch on the upper side.

In an analogous manner, it is also possible to prepare tablets each containing 10 mg of another compound of the formula I according to Examples 1 to 13, which compound may also be in the form of a salt with a base, for example in the form of the disodium salt.

EXAMPLE 19

Gelatine dry-filled capsules, each containing 100 mg of active ingredient, for example 1-(thiazol-2-ylamino)methane-1,1-diphosphonic acid or a salt, for example the sodium salt, thereof, can be prepared in the following manner:

| Composition (for 1000 capsules) | |
| --- | --- |
| active ingredient | 350.0 g |
| microcrystalline cellulose | 30.0 g |
| sodium lauryl sulphate | 2.0 g |
| magnesium stearate | 8.0 g |

The sodium lauryl sulphate is sieved into the active ingredient (lyophilised) through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm mesh width and, after mixing for a further 3 minutes, the mixture is introduced in portions of 390 mg each into size 0 (elongated) gelatine dry-fill capsules.

In an analogous manner, it is also possible to prepare capsules each containing 100 mg of another compound of the formula I according to Examples 1 to 13, which compound may also be in the form of a salt with a base, for example in the form of the disodium salt.

EXAMPLE 20

A 0.2% injection or infusion solution can be prepared, for example, in the following manner:
  active ingredient, for example 1-(thiazol-2-ylamino)-methane-1,1-diphosphonic acid or a salt, for example the sodium or the disodium salt, thereof—5.0 g
  sodium chloride—22.5 g
  phosphate buffer pH 7.4—300.0 g
  demineralised water—to 2500.0 ml The active ingredient is dissolved in 1000 ml of water and filtered through a microfilter. The buffer solution is added and the whole is made up to 2500 ml with water. To prepare dosage unit forms, portions of 1.0 or 2.5 ml each are introduced into glass ampoules (each containing respectively 2.0 or 5.0 mg of active ingredient).

We claim:

1. A heteroarylaminomethanediphosphonic acid of the formula

in which $R_1$ represents an imidazolyl, oxazolyl, or thiazolyl, benzothiazolyl or thiadiazolyl radical that is C-unsubstituted or C-mono- or C-di-substituted by lower alkyl; by lower alkoxy; by phenyl that is unsubstituted or is mono- or di-substituted by lower alkyl, lower alkoxy and/or by halogen; by hydroxy; by di-lower alkylamino; by lower alkylthio and/or by halogen; and that is unsubstituted at a substitutable N-atom which may be present or N-mono-substituted by lower alkyl or by phenyl-lower alkyl that is unsubstituted or is mono- or disubstituted by lower alkyl, lower alkoxy and/or by halogen; and $R_2$ represents hydrogen or lower alkyl, or a salt thereof.

2. A compound as claimed in claim 1, of the formula I in which $R_1$ represents a thiazolyl radical, benzothiazol-2-yl radical, thiadiazolyl radical, oxazolyl radical or benzoxazol-2-yl radical each of which is unsubstituted or is C-substituted by $C_1$–$C_4$-alkyl or by a phenyl radical that is unsubstituted or is mono- or di-substituted by $C_1$–$C_4$-alkyl, $C_1$–$C_4$-alkoxy and/or by halogen; or represents an imidazol-2-yl radical which is unsubstituted or is C-substituted by $C_1$–$C_4$-alkyl or by a phenyl radical that is unsubstituted or is mono- or di-substituted by $C_1$–$C_4$-alkyl, $C_1$–$C_4$-alkoxy and/or by halogen, and/or is N-substituted by $C_1$–$C_4$-alkyl or by a phenyl-$C_1$–$C_4$-alkyl radical that is unsubstituted or is mono- or di-substituted by $C_1$–$C_4$-alkyl, $C_1$–$C_4$-alkoxy and/or by halogen; and $R_2$ represents hydrogen, or a salt thereof.

3. A compound as claimed in claim 1, of the formula I in which $R_1$ represents a thiazolyl radical, a 1-$C_1$–$C_4$-alkylimidazol-2-yl or -4-yl radical or a 1-phenyl-$C_1$–$C_4$-alkyl imidazol-2-yl or -4-yl radical each of which is unsubstituted or is C-substituted by $C_1$–$C_4$-alkyl, by $C_1$–$C_4$-alkoxy, by phenyl, by hydroxy, by di-$C_1$–$C_4$-alkylamino, by $C_1$–$C_4$-alkylthio or by halogen having an atomic number of up to and including 35, and $R_2$ represents hydrogen, or a salt thereof.

4. A compound as claimed in claim 1, of the formula I in which $R_1$ represents a thiazol-2-yl radical that is unsubstituted or is mono- or di-substituted by $C_1$–$C_4$-alkyl or by phenyl, or represents an imidazol-2-yl or radical that is unsubstituted or is mono-substituted in the 1-position by $C_1$–$C_4$-alkyl or by phenyl-$C_1$–$C_4$-alkyl, respectively, or represents an unsubstituted benzoxazol-2-yl or benzothiazol-2-yl radical, and $R_2$ represents hydrogen, or a salt thereof.

5. A compound as claimed in claim 1, wherein $R_1$ denotes a 1-$C_1$–$C_4$-alkylimidazol-2-yl, thiazol-2-yl or 4-$C_1$–$C_4$-alkylthiazol-2-yl radical and $R_2$ denotes hydrogen, or a salt thereof.

6. A compound as claimed in claim 1 being 1-(thiazol-2-ylamino)methane-1,1-diphosphonic acid or a salt thereof.

7. A compound as claimed in claim 1 being 1-(5-methyl-1,3,4-thiadiazol-2-ylamino)methane-1,1-diphosphonic acid or a salt thereof.

8. A compound as claimed in claim 1 being 1-(1,3,4-thiadiazol-2-ylamino)methane-1,1-diphosphonic acid or a salt thereof.

9. A compound as claimed in claim 1 being 1-(1-methylimidazol-2-ylamino)methane-1,1-diphosphonic acid or a salt thereof.

10. A compound as claimed in claim 1 being 1-(3-phenyl-1,2,4-thiadiazol-5-ylamino)methane-1,1-diphosphonic acid or a salt thereof.

11. A compound as claimed in claim 1 being 1-(benzothiazol-2-ylamino)methane-1,1-diphosphonic acid or a salt thereof.

12. A compound as claimed in claim 1 being 1-(benzoxazol-2-ylamino)methane-1,1-diphosphonic acid or a salt thereof.

13. A compound as claimed in claim 1 being 1-(5-methylthiazol-2-ylamino)methane-1,1-diphosphonic acid or a salt thereof.

14. A compound as claimed in claim 1 being 1-(5-ethylthiazol-2-ylamino)methane-1,1-diphosphonic acid or a salt thereof.

15. A compound as claimed in claim 1 being 1-(5-propylthiazol-2-ylamino)methane-1,1-diphosphonic acid or a salt thereof.

16. A compound as claimed in claim 1 being 1-(1,5-dimethylimidazol-2-ylamino)methane-1,1-diphosphonic acid or a salt thereof.

17. A compound as claimed in claim 1 being 1-(5-prop-2-ylthiazol-2-ylamino)methane-1,1-diphosphonic acid or a salt thereof.

18. A compound as claimed in claim 1 being 1-(5-butylthiazol-2-ylamino)methane-1,1-diphosphonic acid or a salt thereof.

19. A compound as claimed in claim 1 being 1-(5-prop-1-ylthiazol-2-ylamino)methane-1,1-diphosphonic acid or a salt thereof.

20. A heteroarylaminomethanediphosphonic acid of the formula

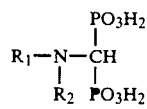

in which $R_1$ represents a benzoxazol-2-yl; benzothiazol-2-yl; benzimidazol-2-yl; 1,3,4-oxadiazol-2-yl; thiadiazolyl; 2H-1,2,4-triazol-3-yl; oxazol-2-yl; thiazol-2-yl or imidazol-2-yl group that is unsubstituted or is C-substituted by lower alkyl; by phenyl that is unsubstituted or is substituted by lower alkyl, lower alkoxy and/or by halogen; by lower alkoxy; by hydroxy; by di-lower alkylamino; by lower alkylthio and/or by halogen; and/or that is N-substituted by lower alkyl; or by phenyl-lower alkyl that is unsubstituted or substituted by lower alkyl, lower alkoxy and/or by halogen; and $R_2$ represents hydrogen or lower alkyl, or a salt thereof.

21. A compound according to claim 1 wherein $R_1$ denotes a 4-$C_1$-$C_4$-alkylthiazol-2-yl radical and $R_2$ denotes hydrogen or a salt thereof.

22. A pharmaceutical composition containing a compound of the formula I as claimed in claim 1, or of a pharmaceutically acceptable salt thereof together with customary pharmaceutical adjuncts.

23. A method of treatment of illnesses that can be attributed to calcium metabolism disorders, characterised in that as claimed in claim 1 a compound of the formula I or a pharmaceutically acceptable salt thereof is administered to a warm-blooded animal in need thereof.

* * * * *